United States Patent [19]
Podlasek et al.

[11] Patent Number: 5,342,755
[45] Date of Patent: Aug. 30, 1994

[54] METHOD FOR THE DETECTION OF ANTI-STREPTOKINASE ANTIBODIES

[75] Inventors: Stanley J. Podlasek, McLean, Va.; Richard A. McPherson, Solana Beach, Calif.

[73] Assignee: Georgetown University, Washington, D.C.

[21] Appl. No.: 777,319

[22] PCT Filed: May 30, 1990

[86] PCT No.: PCT/US90/03080
§ 371 Date: Jan. 31, 1992
§ 102(e) Date: Jan. 31, 1992

[87] PCT Pub. No.: WO90/15153
PCT Pub. Date: Dec. 13, 1990

Related U.S. Application Data

[63] Continuation-in-part of Ser. No. 360,822, Jun. 2, 1989, abandoned.

[51] Int. Cl.$^5$ .............. C12Q 1/00; C12Q 1/56; G01N 33/53; G01N 33/564
[52] U.S. Cl. .................. 435/7.1; 435/7.71; 435/7.92; 435/13; 435/975; 436/69; 436/506; 436/538
[58] Field of Search ............ 435/7, 7.1, 7.71, 7.92, 435/13, 975; 436/506, 538, 69

[56] References Cited

U.S. PATENT DOCUMENTS 4,376,110  3/1983  David et al. .............. 436/513
4,690,907  9/1987  Hibino et al. ............. 436/514

OTHER PUBLICATIONS

Edelberg, et al., *Biochemistry*, vol. 28, pp. 2370–2374, 1989.
Applicant's Ref. AR3; Podlasek, et al., (*Clin. Chem.* 34:1283 (1988)).
*Clinical Chemistry*, 35/1, 69–73 (1989), Podlasek et al.
*Clinical Chemistry*, 31/1, 527–532 (1985), Podlasek et al.
*Clinical Investigations*, 37, 1306–1315, 1958, Fletcher et al.

*Primary Examiner*—Margaret Parr
*Assistant Examiner*—Bradley L. Sisson
*Attorney, Agent, or Firm*—Sterne, Kessler, Goldstein & Fox

[57] ABSTRACT

A method is described for the detection of anti-streptokinase antibodies in a sample which comprises detection of a complex between lactate dehydrogenase, streptokinase, and antistreptokinase antibodies. The method is useful for the detection of antistreptokinase antibodies in the serum of patients prior to clinical streptokinase administration.

9 Claims, 5 Drawing Sheets

METHOD FOR THE DETECTION OF ANTI-STREPTOKINASE ANTIBODIES

CROSS-REFERENCE TO RELATED APPLICATIONS

This application is a Continuation-In-Part application of U.S. Ser. No. 07/360,822, filed Jun. 12, 1989, now abandoned.

FIELD OF THE INVENTION

This invention is directed to methods for the detection of antistreptokinase antibodies, that is, antibodies which recognize streptokinase and/or a complex of streptokinase with another protein. The methods of the invention are based upon the ability of streptokinase to simultaneously bind to other proteins such as lactate dehydrogenase (LD) subunit M and to antistreptokinase antibodies. Specifically, the addition of exogenous streptokinase to samples containing antistreptokinase antibodies and a streptokinase binding protein results in the formation of a three-part complex which can be revealed by reporter methods which detect the streptokinase binding protein or its subunits. The methods of the invention are useful as diagnostic tests for the detection of serum antibodies to streptokinase.

BACKGROUND OF THE INVENTION

Present day treatment for acute myocardial infarction entails intravenous administration of a thrombolytic drug within the first few hours after onset of symptoms to break up (lyse) blood clots within coronary arteries thereby reversing damage to the affected heart muscle. There are two major thrombolytic drugs now available, streptokinase and tissue plasminogen activator (TPA).

The activation of plasminogen by either streptokinase or TPA results in the formation of plasmin, a proteolytic enzyme that degrades fibrin, the principal component of the lattice which holds a blood clot together.

Streptokinase is a naturally occurring product from the bacteria streptococci. Because streptokinase is a bacterial product and an antigen, many individuals who have had previous streptococcal infections (e.g., strop throats) have anti-streptokinase antibodies in their blood. These antibodies neutralize streptokinase when it is administered as a drug (Brogden, R. N., et al., Drugs: 5:357–445 (1973)). Anti-streptokinase titers between 2 to 402 U/ml in a random sample of 120 people has been reported (Bachmann, F., J. Lab. Clin. Med. 72:228 (1968)). Streptokinase is biochemically inert when bound to this antibody and the complex of streptokinase and antibody is rapidly cleared from the circulation (Fletcher, A. P. et al., Clin. Invest. 37:1306 (1958)). Such antistreptokinase antibodies may account for some treatment failures of streptokinase in myocardial infarction due to inadequate dosing with the drug.

It is necessary to begin thrombolytic therapy early after onset of myocardial infarction (within 4 hours) to achieve satisfactory clinical results. Consequently, the choice of which drug to use and how much to use should be made quickly. For effective therapy when streptokinase is chosen, the dose of streptokinase must begin with a dosage in excess of that required to neutralize endogenous circulating antibodies to streptokinase (Bfogden, R. N., et al,, Drugs: 5:357–445 (1973)). Doses which are not in excess of the amount required to neutralize these endogenous antibodies are pharmacologically inactive. It is critical to determine the proper dose for streptokinase therapy. Doses which are too high may lead to the formation of excessive plasmin and result in the depletion of additional proteins which plasmin also degrades, such as circulating fibrinogen and clotting factors V and VIII. Thus, with too much streptokinase there is a risk of hemorrhage. When the hemorrhage occurs in the central nervous system, grave neurological impairment or death usually results (Braunwald, E. et al., J. Am. Coll. Cardiol. 10:970 (1987); Haber, E. et al., Science 243:51 (1989)).

Because there is such individual variability in the levels of antistreptokinase antibodies, a rapid determination of the presence of significant amounts of anti-streptokinase antibodies in a patient would be very useful in guiding medical decisions concerning the dosage of streptokinase needed for therapeutic treatment. With the knowledge that antistreptokinase antibodies are present, an appropriate initial neutralizing dose may be administered, followed by an infusion of the drug in an amount sufficient to maintain the level of free streptokinase required for the induction of a thrombolytic state.

Such an assay would also be useful as part of routine cardiac risk assessment profiling, especially, after a patient has been treated with streptokinase. Eight to nine days after treatment, the titer of antistreptokinase antibodies rapidly rises 50-fold to 100-fold in most patients, only returning to pretreatment levels 4–6 months later (Schmutzler, R. et al., Thrombolytic Therapy, in Poller Recent Advances in Blood Coagulation, p. 324, Churchill, London, 1969). Consequently, it is critical to know the titer of streptokinase antibodies in these patients before repeating a course of streptokinase within a few months of the original treatment.

Further, just as cholesterol is used as a screening test for risk of developing heart disease, it is desirable to routinely prescreen individuals for antistreptokinase antibody status on a regular basis. The results of such a prescreen would be of value for individuals who wish to know if streptokinase would be efficacious in treating their future heart-attacks.

Thus a need exists for a rapid, economical test for antistreptokinase antibodies.

It is known that the bacterial thrombolytic agent streptokinase binds to human, porcine, and chicken LD isoenzyme subunit M, but not to the H or C subunits (Podlasek, S. J. et al., Clin. Chem. 35:69–73 (1989)). There is amino acid sequence homology between LD and the streptokinase binding site on plasminogen to account for this interaction. The binding of streptokinase to LD subunit M results in the formation of a streptokinase-LD complex in serum that contain LD activity (Podlasek, S. J. et al., Clin. Chem. 35:69–73 (1989)). However, it has not previously been known to use the affinity of streptokinase for LD as the basis for the determination of antistreptokinase antibodies in the serum of an individual.

SUMMARY OF THE INVENTION

A simple and unique method by which to determine the presence of antistreptokinase antibody in a subject is presented. This method further detects antibody which reacts with a complex between streptokinase and other proteins.

A previous development that demonstrated a similarity between the enzyme lactate dehydrogenase (LD) and plasminogen (the natural target of streptokinase)

culminated in the present invention which provides methods based on the interaction between streptokinase and a streptokinase binding protein (such as subunit M-containing LD). The method of the invention may be used as the basis for an assay to determine the presence of antistreptokinase antibodies in a subject's serum. The method is unique in that it takes advantage of this previously unrecognized and unsuspected structural similarity between LD and plasminogen. The method utilizes reagents, procedures, and technologies currently available in virtually all hospital laboratories, such as, for example, immunological, electrophoretic and chromatographic techniques. It is a rapid, convenient, and simple method.

By the present invention, diagnostic assays involving the use of LD isoenzyme electrophoresis have been developed for the detection of antibodies to streptokinase in samples suspected of containing antibodies against streptokinase.

BRIEF DESCRIPTION OF THE DRAWINGS

FIG. 1A: lane a, serum containing normal LD isozymes 1, 2, 3, 4, and 5; lane b, serum plus streptokinase; lane c, streptokinase alone; lane d, semi -purified LD1; lane e, LD1 plus streptokinase; lane f, semi -purified LD5; lane g, LD5 plus streptokinase; lane h, serum al one. FIG. 1B: lane a, serum alone; lane b, semi-purified LDX; lane c, streptokinase alone; lane d, LDX plus streptokinase; lane e, serum alone.

DESCRIPTION OF THE PREFERRED EMBODIMENTS

Figure 1A:
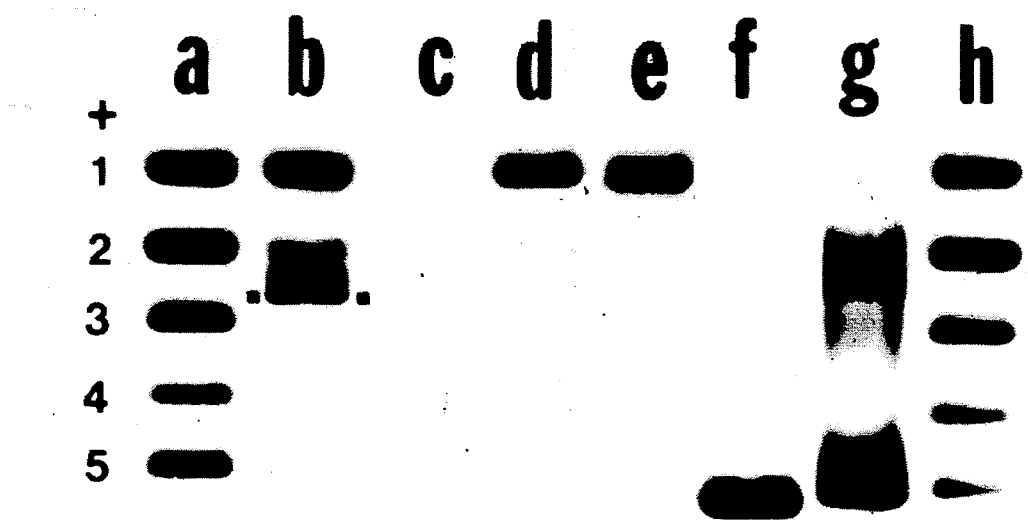
FIGS. 1A and 1B show is a gel electrophoresis pattern showing the interaction of streptokinase with different LD subunits. The concentration of streptokinase added was 15,000 IU/ml. A tight band (complex) of LD activity remained at the electro-phoretic origin (arrow) when streptokinase was mixed with serum (markers in FIG. 1A, lane b). Streptokinase altered the mobility of purified LD5 but not that of LD1 or LDX.

The invention comprises methods which detect antistreptokinase antibodies in a sample by the ability to form a complex between such antistreptokinase antibodies, streptokinase and a streptokinase binding protein other than an antibody. This complex is herein termed the "three-part complex."

By the term antistreptokinase antibody is meant two types of antibodies: antibodies which recognize (bind to) streptokinase and antibodies which recognize a complex containing streptokinase and a second (non-antibody) protein.

In one embodiment, the non-antibody streptokinase binding protein is a protein which contains the streptokinase consensus binding sequence Phe/Cys-Pro-Lys-any/none-Arg-Val-Ile/Val-Gly-any/none-Gly-Cys such as, for example, lactate dehydrogenase subunit M, plasminogen, plasmin, Lp(a).

By a "complex" (between proteins) is meant that two or more proteins are associated together in a non-covalent manner, through hydrogen bonding, ionic attraction and other noncovalent means, with such an affinity that the proteins in such complex are capable of extraction, analysis and measurement as a singular complex or entity. The formation of a "streptokinase binding protein-streptokinase-antistreptokinase antibody" complex in samples of the serum of an individual may be used as a rapid and specific assay for the presence of such antistreptokinase antibodies in the serum of an individual.

In a preferred embodiment, LD which possesses at least one M subunit is used as the non-antibody binding protein. The complex which forms between streptokinase and LD upon the addition of exogenous streptokinase to a sample containing LD possesses such affinity that, if streptokinase antibodies are present in the sample, they also bind to the LD-streptokinase complex without dissociating it.

The presence of the three part streptokinase binding protein-streptokinase-antistreptokinase antibody complex can be detected by any technique that reveals the presence of the complex. For example, when LD is used as the streptokinase binding protein, the three part complex can be detected by any technique that reveals the size, or a change in the size, of the LD isozymes in a serum sample, or changes in a distribution pattern of LD isozymes which occurs in the presence of streptokinase and serum. Thus the presence of streptokinase antibodies may be predicted from physical properties of the LD isozyme pattern, for example, size or charge, after addition of streptokinase to a sample of the patient's serum.

The enzyme lactate dehydrogenase is a tetrameric enzyme which exists in at least five isoenzymic forms in an individual. Each subunit of the enzyme has a molecular weight of approximately 33,500 daltons but the isozymes vary in their content of one of three subunit types called type M, H or C. Serum LD isozyme analysis is frequently used in medical diagnosis and is a routine procedure in clinical laboratories. The electrophoretic separation of LD isozymes from serum may separate five bands of LD activity representing LD1, LD2, LD3, LD4 and LD5, respectively, with LD1 migrating fastest towards the anode and LD5 migrating fastest towards the cathode. LD1 is a tetramet of four H chains and LD5 is a tetramet of four M chains. The tetrameric structures of LD2, LD3 and LD4 consist of a mixture of subunit types, $H_3M$, $H_2M_2$, and $HM_3$, respectively. The C subunit is found in LD isolated from spermatozoa, called LDX.

To practice the methods of the invention it is necessary to provide conditions which allow a complex between streptokinase and the streptokinase binding protein to occur. Such a complex will occur if streptokinase is added to serum and the serum is allowed to incubate at room temperature for at least 15 minutes to one hour. If antistreptokinase antibodies are present, the binding of antistreptokinase antibodies to the streptokinase-streptokinase binding protein complex may occur concurrently with the binding of streptokinase to streptokinase binding protein.

Alternatively, a prebound complex of streptokinase-streptokinase binding protein can be added directly to the serum. In this case, the length of time of the incubation need only be long enough to allow for binding of the anti-streptokinase antibodies to the streptokinase-streptokinase binding protein complex, for example, 15 min. to one hour.

When LD is used as the streptokinase binding protein, if desired, exogenous LD containing a M subunit may be added to the serum so as to ensure that sufficient M-containing LD is present in the serum to be tested.

In a preferred embodiment, the final concentration of streptokinase in the assay is approximately 1500 IU/ml to 150,000 IU/ml, and most preferedly, 15,000 IU/ml. The streptokinase is added to a small sample of serum, preferably less than 0.5 ml, incubated for 15-60 minutes, and analyzed (using, for example, electrophoresis or column chromatography techniques) under conditions that separate LD isozymes or complexes thereof. If electrophoresis is used, then after staining to inspect the resulting electrophoretic pattern, the presence or absence of antistreptokinase antibodies can be visually determined. Preferedly, the staining is an activity stain so that only protein bands containing some LD activity are revealed.

Any protocol which allows for the separation or detection of the three-part complex and/or LD isozymes (if LD is used as the reporter and as the streptokinase binding protein) is useful for the methods of the invention. Especially, any chromatographic, ELISA, or electrophoretic protocol which will differentiate between the complex containing streptokinase-LD and a three-part complex containing antistreptokinase antibody-streptokinase-LD is useful in the methods of the invention. One of skill in the art can design conditions and gel formulae that allow for this distinction. Gel electrophoresis is reviewed in *Gel Electrophoresis of Proteins, A Practical Approach*, B. D. Hames et al., eds., IRL Press, Washington, 1981.

In a preferred embodiment, when LD is used as the streptokinase binding protein and electrophoresis through a gel matrix is used to analyze the sample, the gel porosity and electrophoretic buffer conditions are such that migration of the antistreptokinase antibody-streptokinase-LD complex into the gel occurs only to a small extent or does not occur and the three-part complex remains at, or essentially at, the origin of the gel. The origin of the gel is that location where the sample was originally applied to the gel before electrophoresis. Complexes which are too large to migrate very far into the gel's structure, or which are electrically neutral relative to the anode and cathode, remain at, or essentially at, the origin. Generally such protein will not be washed away in developing (staining) the gel but will remain bound or entangled with the gel matrix at the origin of the gel. An example of a preferred gel with an appropriate porosity is a 1% agarose gel. Electrophoresis of a 1% agarose gel in pH 8.2 barbital buffer at 100 V for a time sufficient to separate LD isozymes (for example, 20-28 min with the Beckman Paragon$^R$ electrophoresis system), followed by staining of LD activity in the gel reveals the presence of antistreptokinase antibodies by the presence of a precipitate of an LD complex at the origin of the electrophoretic gel. If no anti-streptokinase antibodies are present, the complex of streptokinase with LD migrates into the gel and does not precipitate at, or remain at, the origin.

Colorimetric staining for LD activity may be performed by, for example, incubating the electrophoresed gel in contact with substrate containing an appropriate amount of the LD substrates, for example, approximately 208 mM lithium lactate and 5.6 mM NAD+. The NADH generated due to LD activity in converting the lactate and NAD to pyruvate and NADH will appear at the site of the LD isozyme in the gel. The NADH and thus the site of the LD activity, can be colorimetrically detected with a dye such as p-nitro blue tetrazolium (NBT) which is reduced to a colored product in the presence of NADH. For example, the addition of 1.9 g/L of NBT in the presence of 0.33 mmol/L phenazine methosulfate (PMS) results in the formation of a blue formazan indicator pigment at the site of the LD isozyme in the gel. Gels developed in this manner for enzyme activity can be fixed in 50 mL/L acetic acid solution and heat dried.

Isoenzyme protein may also be identified with fluorescence, chemiluminescence, radiolabelling, or immunological techniques.

Examples of gel matrices which can be used for the methods of the invention include agarose, polyacrylamide, starch, and combinations thereof. The conditions for separating the LD isozymes by electrophoresis are well known in the art and have been reviewed in, for example, Moses, G. C., *Clin. Chem* 34:1885-1890 (1988); McKenzie, D. et al., *Clin. Chem.* 29:189-195 (1983); and Roman, W., *Enzymologia* 36:189-219 (1969)).

Examples of buffers which can be used to perform LD isozyme analysis in agarose gels include barbital, barbital/EDTA, Tris-barbital, barbital/AMPD (2-amino-2-methyl-1,3-propanediol, and MOPSO (3-(N-morpholino)-2-hydroxypropanesulfonic acid). Examples of buffers which can be used to run LD isozyme analysis with acetate gels includes tris-barbital.

A summary of the assay conditions for the various electrophoretic support media and buffer systems is presented in Moses, G. D., et al., *Clin. Chem.* 34:1885-1890 (1988), incorporated herein by reference.

Commercially available gel systems are also useful in the methods of the invention such as the Paragon ® gel system provided by Beckman.

The presence of antistreptokinase antibodies may also be detected by assaying LD enzyme activity in the serum before and after the addition of concentrations of streptokinase similar to those used for electrophoretic determination of antibodies, 1500 IU/ml to 150,000 IU/ml, and most preferedly, 15,000 IU/ml final concentration. It has been discovered that LD activity decreases when trapped in a complex containing streptokinase and antistreptokinase antibodies. Therefore, a reduction of LD activity after addition of streptokinase is indicative of the presence of antistreptokinase antibodies in the sample.

The presence of the antistreptokinase antibody-streptokinase-LD complex may also be assayed by a method which relies on column chromatography or filtration (either with a resin or a microfilter) to separate the antibody-containing LD complexes from complexes which do not contain antibody. For example, one of skill in the art can design chromatographic conditions which separate non-antibody-containing LD complexes with a molecular weight of approximately 187,000 daltons (the sum of the molecular weight of the LD tetramet, 140,000 daltons and the molecular weight of streptokinase, 47,000 daltons) from larger complexes which would include the antibody. Such chromatography may be performed with any suitable chromatographic matrix, especially those which separate by size, such as, for example, Sepharose ®, and Sephadex ® and especially Sephadex ® G-200. If the fraction containing serum proteins of molecular weight greater than 187,000 daltons is void of LD activity, the serum does not contain antistreptokinase antibodies. The appearance of LD activity in a fraction of molecular weight significantly greater than 187,000 daltons would indicate the presence of the LD-streptokinase-antistreptokinase complex and of anti-streptokinase antibodies in the serum of the individual being tested.

Any streptokinase or portion thereof possessing affinity for both the antibodies found in serum and a non-antibody binding protein, especially LD subunit M, is useful in the methods of the invention. Such streptokinase is available commercially, for example, from Boehringer Mannheim Biochemicals, Indianapolis, Ind. and Sigma Chemical Co., St. Louis, Mo. Preparations containing streptokinase in a composition which further contains albumin or collagen are also useful in the methods of the invention, for example, Streptase ® from Hoechst-Roussel Pharmaceuticals, or Kabikinase ® from Kabi-Vitrum.

In addition, the materials for use in the assays of the invention are ideally suited for preparation of a kit. Such a kit may comprise a carrier means being compartmentalized to receive in close confinement one or more container means such as vials, test tubes, and the like. Each of said container means comprises one of the separate elements to be used in the method.

For example, one of said container means may comprise streptokinase. A second container may comprise a detection system for LD.

The carrier may also contain, in addition, a plurality of containers each of which comprises different, predetermined and known amounts of buffer and other solutions, gels or resins necessary for the separation of LD complexes or isozymes.

In the practice of this invention, the presence of antistreptokinase antibodies may be detected in biological fluids and tissues. Any sample containing the unknown amount of antistreptokinase antibodies can be used. Preferably, serum is used. Normally, a sample is a liquid such as, for example, serum, urine, saliva, tear drops, cerebrospinal fluid, blood, plasma and the like. A solid or semi-solid such as, for example, tissues, feces, and the like may be used if they are first homogenized or otherwise placed in liquid suspension. Such methods are known in the art. In addition, it is also known in the art that antibodies to streptokinase may be present in a human's or animal's biological fluids or tissue, without such human or animal suffering from a streptococcal infection or previous exposure to streptokinase.

Any means of detecting LD and especially LD subunit M may be used. For example, detectably labelled antibodies to the streptokinase binding protein or three-part complex, and especially to LD, or LD subunit M, may be used to reveal the presence of the complex between LD and streptokinase, and the presence or absence of the antistreptokinase antibodies.

In addition, one of ordinary skill in the art would understand that the methods of the invention may be used to identify disease processes caused by or associated with an autoimmune response to the complexes as described herein and especially to identify the presence, in the serum of patients, of antistreptokinase antibodies which specifically recognize a complex between streptokinase and a serum streptokinase binding protein.

The following examples are given to further illustrate the present invention and in no way are intended to limit the scope of the present invention unless otherwise stated.

EXAMPLES

Materials and Methods

1. Samples. Serum samples from 10 ambulatory patients were pooled, after completion of routine chemistry analyses, for use in mixing studies with streptokinase. Serum samples with high concentrations of LD isoenzyme 1 and of creatine kinase isoenzymes MM and MB were available after routine testing of patients with acute myocardial infarction. Normal human liver and testes were obtained at autopsy, within 24 h of death. Both porcine and chicken heart and skeletal muscle were obtained as fresh, uncooked meat from a food store.

2. Reagents. Streptase ® (containing streptokinase, human albumin, and collagen peptides) was from Hoechst-Roussel Pharmaceuticals, Inc., Somerville, N.J. 08876. Kabikinase ® (containing streptokinase and human albumin) was from Kabi-Vitrum, Inc., Alameda, Calif. 94501. Non-pharmaceutical streptokinase was obtained from Boehringer Mannhelm Biochemicals. Alteplase recombinant Activase ® (tissue plasminogen activator, TPA) was from Genentech, Inc., South San Francisco, Calif. 94080. Urokinase (derived from human kidney cells) QAE Sephadex (Q50-120), and NAD+ (grade III-beta) were from Sigma Chemical Co., St. Louis, Mo. 63178. Sephadex G-200 was from Pharmacia Fine Chemicals, Inc., Piscataway, N.J. 08854. Polygeline TM modified collagen was from Calbiochem-Behring Diagnostics, La Jolla, Calif. 92037. Isomune-LD TM was from Roche Diagnostics, Nutley, N.J. 07110. The Paragon TM electrophoresis system with LD, creatine kinase, and serum protein (SPE)

agarose gels, barbital buffers, enzyme substrates, and developing reagents as well as reagents for measurement of total LD activities in the Astra ™ automated chemistry analyzer were from Beckman Instruments, Inc., Brea, Calif. 92621.

3. Methods. For LD isoenzyme analysis, creatine kinase isoenzyme analysis, and serum protein electrophoresis Paragon gels and reagents were used according to the manufacturer's instructions (Beckman Instruction Book No. 015-556462-G (for LD), No. 015-556461-H (for creatine kinase), and No. 015-556458-G (for serum protein) from Beckman Instruments, Inc., Diagnostic Systems Group, Brea, Calif.).

LD isoenzymes were extracted by mincing the tissue in a volume of 145 mmol/L sodium chloride equal to the volume of the tissue and subsequently clarified by centrifugation at 5000×g. LD5 was semi-purified by passing liver extract through a QAE-Sephadex anion-exchange column (bed volume 45 mL, 27 cm high, flow rate approximately 30 mL/h) equilibrated in 20 mmol/L Tris HCl, pH 8.2 (buffer A). LD5 passed directly through this column, free of LD1-LD4. LD1 was semi-purified by loading serum rich in that isoenzyme onto a similar column, washing off LD2-LD5 with buffer A containing 215 mmol of sodium chloride per liter, and then eluting LD1 free of the other LD isoenzymes with buffer A containing 260 mmol of sodium chloride per liter (Podlasek, S. J. et al., *Clin. Chem.* 31:527-32 (1985); Hsu, M-Y. et al., *Clin. Chem.* 25:1453-8 (1979)).

To semi-purify LDX (LD from spermatozoa which contains a subunit called "subunit C"), one volume of testicular extract was mixed with four volumes of Isomune-LD solution A (goat anti-human LD-M antibody) and then immunoprecipitated with an equal volume of Isomune-LD solution B (polymer-bound donkey anti-goat immunoglobulin) to remove all M-subunit-containing LD isoenzymes. LDX was then separated from LD1 by QAE anion-exchange column chromatography as above. LD1 was retained on the column, and the LDX was separately eluted with buffer A containing 140 mmol of sodium chloride per liter.

Individual fractions of LD1, LD5, and LDX were dialyzed against phosphate-buffered saline (10 mmol of sodium phosphate, pH 7.2, and 149 mmol of sodium chloride per liter) before mixing with streptokinase (see below).

Gel filtration for molecular sizing was done with a Sephadex G-200 column (bed volume 75 mL, 55 cm high, flow rate approximately 45 mL/h) equilibrated with the phosphate-buffered saline. One ml fractions were collected.

EXAMPLE 1

Interaction of Streptokinase with LD Isoenzymes in Serum

Pooled serum (nine volumes) containing all five LD isoenzymes was mixed with one volume of streptokinase (final concentration 15000 int. units/mL), incubated for 1 h at room temperature, and then electrophoresed and developed for LD activities. This manipulation resulted in marked alteration of the isoenzyme pattern, with complete removal of the major M-subunit-containing isoenyzmes (LD3, LD4, and LD5). A large amount of LD activity remained at the origin of application, suggesting the formation of an insoluble precipitate (FIG. 1A, lane b). Each of the three different streptokinase preparations produced the same effect on LD isoenzymes. The two pharmaceutical preparations were also free of endogenous LD activity (FIG. 1A, lane c). As a control, the stabilizing components in these streptokinase preparations, mixed separately with serum to achieve similar concentrations, showed no interaction with LD. Mixtures of streptokinase and human serum samples were also electrophoresed and evaluated for creatine kinase isoenzymes and for total stainable proteins. There were no alterations in electrophoretic migration of creatine kinase isoenzymes or of the major serum proteins resulting from the addition of streptokinase. These findings established that streptokinase interacted with human LD in a specific and significant manner without completely inactivating it.

EXAMPLE 2

Streptokinase Mixed with Individual LD Isoenzymes

Figure 1B:
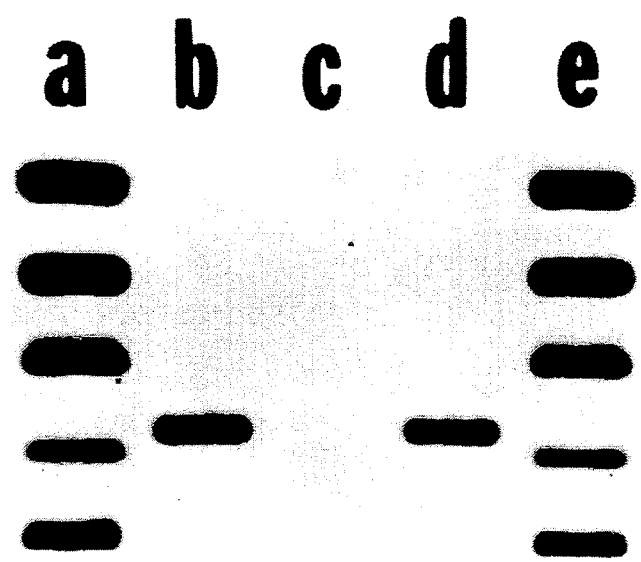

Semi-purified LDI or LD5 (nine volumes) was mixed with one volume of streptokinase (final concentration 15000 IU/mL) and subjected to electrophoretic analysis to determine whether binding was specific for the H or M subunit of LD. Addition of streptokinase to LD1 (H tetramet) did not alter that isoenzyme's mobility (FIG. 1A, lane e) indicating that streptokinase and the H subunit did not interact. In contrast, addition of streptokinase to LD5 resulted in a major alteration of that isoenyzme's electrophoretic migration (FIG. 1A, lane g), indicating substantial interaction between streptokinase and the M subunit. Mixtures of streptokinase with semi-purified human LDX showed no interaction of LD subunit C with streptokinase (FIG. 1B, lane d). Thus the interaction of streptokinase with human LD was specific for the M subunit alone.

EXAMPLE 3

Different Streptokinase Concentrations in Serum

Figure 2:
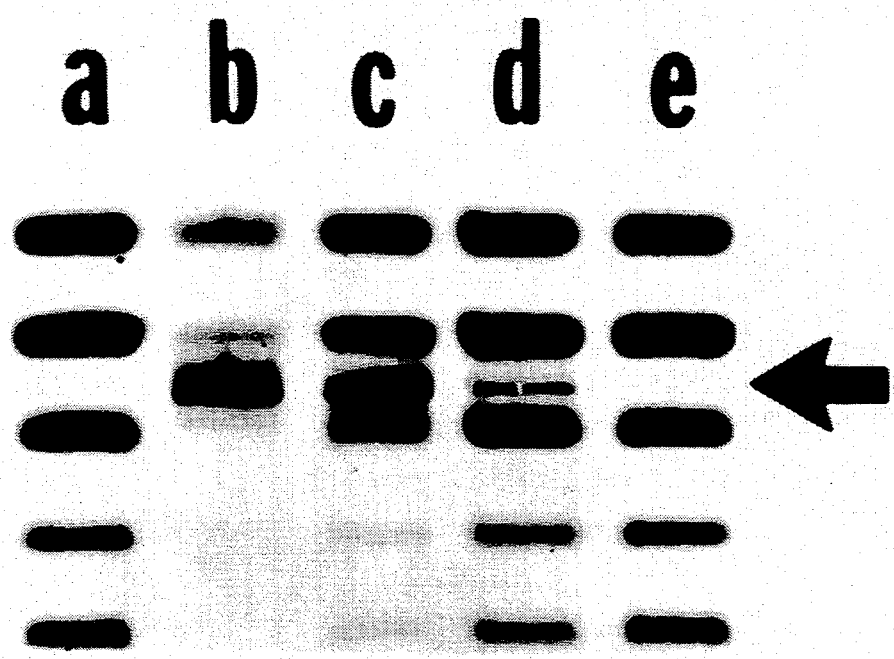
FIG. 2 is a gel electrophoretic pattern showing the interaction of various streptokinase concentrations with LD isozymes in serum. Normal serum was mixed with streptokinase for one hour, electrophoresed, and developed for LD activity. The concentrations of streptokinase in each mixture were: lane a, none; lane b, 15,000 IU/ml; lane c, 7500 IU/ml; lane d, 150 IU/ml. The highest concentration of streptokinase trapped a large amount of LD activity at the origin (arrow).

When serum (nine parts), containing antistreptokinase antibodies, was mixed with different concentrations of streptokinase (one part) before electrophoresis, there was dose-dependent deposition of LD activity at the origin of application, indicative of the formation of the LD-streptokinase-antistreptokinase antibody complex (FIG. 2). At each concentration of streptokinase, there was preferential depletion of the M-subunit-containing isoenzymes of LD. At the highest concentration of streptokinase (FIG. 2, lane b), it appeared that less of the entire sample was able to enter the gel, because of the presence of a physical barrier due to the large amounts of the LD-streptokinase-antistreptokinase antibody complex.

EXAMPLE 4

Sizing of the Complexes

Figure 3:
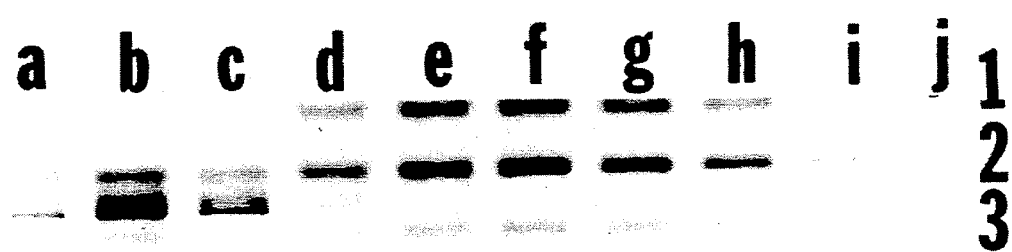
FIG. 3 is a gel electrophoretic pattern showing a comparative sizing of LD streptokinase molecular complex by gel filtration. A 1 ml sample, 0.9 ml of serum plus 0.1 ml of streptokinase (final concentration 7500 IU/ml), was applied to a Sephadex G-200 column and eluted with phosphate-buffered saline. One ml fractions were collected. After a void volume of approximately 5 ml, the streptokinase-LD complexes eluted in fractions 13-15 (lanes a-c) followed by normally migrating LD isozymes (primarily LD1, 2 and 3, as marked) in fractions 16-21 (lanes d-i). Arrow indicates the origin.

The LD-streptokinase-antistreptokinase antibody complexes formed in serum were evaluated by gel filtration, using Sephadex G-200. The fractions obtained from chromatographing a serum-streptokinase mixture were analyzed for LD isoenzyme content by electrophoresis. The complexes (precipitate at electrophoretic origin in FIG. 3, lanes a–c) were eluted after the void volume, but before the normal tetrameric LD isoenzymes (FIG. 3, lanes d–i). This result indicated that the interaction between LD (tetramet molecular size, 140 kDa) and streptokinase (47 kDa) produced a higher-molecular-mass complex and that streptokinase did not simply degrade LD into a smaller non-migrating form.

In the presence of LD2-LD5, which contain different numbers of M subunits, the complexes formed with streptokinase are likely to be heterogeneous, with some very high-mass complexes perhaps being trapped on the column and not detected in this analysis.

EXAMPLE 5

Effect of Urokinase and Tissue Plasminogen Activator

The other fibrinolytic agents, urokinase and TPA, which bind to the same site on plasminogen as does streptokinase, were also added to serum to test for binding to LD. They failed to demonstrate any interaction with LD under conditions similar to those used with streptokinase.

EXAMPLE 6

Comparison of Plasminogen and LD Sequences

The region of plasminogen where streptokinase binds consists of a small loop of amino acids held together by a cysteine-cysteine linkage at its base (amino acid residues 557 to 565) (Collen, D., Thromb. Haemost. 43:7-89 (1980)). A search of known LD sequences (Eventoff, W. et al., Proc. Natl. Acad. Sci. USA 74:2677-81 (1977); Tsujibo, H. et al., Eur. J. Biochem. 147:9-15 (1985); Millan, J. L. et al., Proc. Natl. Acad. Sci. USA 84:5311-15 (1987)) revealed a single region of homology between LD (amino acid residues 153 to 162 according to the numbering for human subunit LD-M) and the streptokinase-binding site on plasminogen (Table 1). Within this region, amino acid residues 156 to 162 are completely conserved in human LD-M and LD-C (the subunit of LDX), in porcine LD-M and LD-H, and in chicken LD-M and LD-H (sequence data were not available for human LD-H). These animal sources of LD were also tested for binding and found that streptokinase interacted strongly with LD-M from all three species (human, porcine, and chicken). However, under the experimental conditions used in this study, streptokinase failed to bind to LD-H from any of these species.

TABLE 1

Comparison of Amino Acid Sequences in the Region of Homology between Plasminogen (Residues 557-565) and LD Subunits (Residues 152-162)

| Human plasminogen | Human | | Porcine | | Chicken | |
|---|---|---|---|---|---|---|
|  | LD-M | LD-C | LD-M | LD-H | LD-M | LD-H |
| Lys | Ser | Ser | Ser | Ser | Ser | Ser |
| Lys | Gly | Gly | Gly | Gly | Gly | Gly |
| 557-CYS | 152-Phe | Leu | Phe | Leu | Phe | Leu |
| GLY | Lys | Val | Lys | Lys | Lys | Lys |
| — | Asn | Thr | Asn | His | His | His |
| ARG | ARG | ARG | ARG | ARG | ARG | ARG |
| VAL | VAL | VAL | VAL | VAL | VAL | VAL |
| VAL | ILE$^a$ | ILE | ILE | ILE | ILE | ILE |
| GLY | GLY | GLY | GLY | GLY | GLY | GLY |
| — | Ser | Ser | Ser | Ser | Ser | Ser |
| GLY | GLY | GLY | GLY | GLY | GLY | GLY |
| 565-CYS | 162-CYS | CYS | CYS | CYS | CYS | CYS |
| Val | Asn | Asn | Asn | Asn | Asn | Asn |
| Ala | Leu | Leu | Leu | Leu | Leu | Leu |
| His | Asp | Asp | Asp | Asp | Asp | Asp |
| B$^b$ | B | NB$^c$ | B | NB | B | NB |

Amino acids in all upper-case letters indicate homology with the streptokinase-binding region of human plasminogen.
$^a$Isoleucine is considered similar to valine.
$^b$B: binds to streptokinase.
$^c$NB: does not bind to streptokinase.

Human LD-C and porcine LD-H, neither of which interact with streptokinase, have sequences differing from that of human LD-M at amino acid residues 152, 154, and 155. The phenylalanine at position 152 is common to all three binders whereas the nonbinders all have leucine at position 152. This finding suggests that the phenylalanine at position 152 is pivotal for streptokinase binding, perhaps because of its relative bulk (compared with leucine in the nonbinders) and as such is somewhat homologous to cysteine at position 557 in plasminogen.

At position 154, lysine is common in both binders and one nonbinder (the other nonbinder, porcine LD-H, has a valine at position 154), suggesting that the amino acid at this position is not critical to streptokinase interaction. At position 155, one nonbinder has threonine (human LD-C) and the other has the positively charged histidine (porcine LD-H), compared with asparagine in the binders. These differences do not (porcine LD-H and chicken LD-H) have the same amino acids at positions 154 (lysine) and 155 (histidine). However, in comparison with the plasminogen sequence of nine amino acid residues from 557-cysteine to 565-cysteine, the homologous stretch in LD-M extends for 11 consecutive residues from 152-phenylalanine to 162-cysteine. In plasminogen, the bonding of the two cysteines probably holds the loop from 557 to 565 in a tight conformation. A similar conformation might arise in LD-M by more gentle bending of a slightly longer peptide loop not held together with a disulfide bond. In order to achieve the same orientation at the tip of the loop (arginine-valine-isoleucine/valine) in relation to its stem and with similar directions of the peptide bond angles, an extra amino acid on one side (160-serine) must be balanced by insertion of an additional amino acid on the other side of the loop. Thus the requirement for an amino acid at position 155 may be to occupy space rather than to contribute a specific side group. These findings collectively suggest the recognition unit for streptokinase binding is approximately Phe/Cys—Pro—Lys—any/none—Arg—Val—Ile/Val—Gly—any/none—Gly—Cys
  1        2     3       4        5     6      7       8       9         10     11

(i.e., either the sequence of all 11 amino acids or the sequence without residues 4 and 9).

Binding by streptokinase is potentially bivalent, owing to an internal duplication, with each half of the molecule homologous to the structure of a serine protease (Jackson, K. W., Biochemistry 21:6620-5 (1982)). Each potential binding site on streptokinase includes the serine and aspartate, but not the histidine characteristic of the active site of serine proteases. The interaction of bivalent streptokinase with tetrameric LD would allow for very long chains or a matrix of complex to form. Such extensive complexes are consistent with the precipitate that remains at the electrophoretic point of application (FIG. 2). In a patient these macro-complexes could be phagocytosed by cells of the immune system, thereby potentiating the induction of an autoimmune response against LD-M. Plasminogen and other molecular species that are only univalent could also participate in the matrix (as chain terminators) and thus be presented to the immune system as well in association with the foreign immunogen, streptokinase.

The occurrence of this binding sequence in both LD and plasminogen is probably fortuitous, because these two proteins have no other significant homologies and are probably otherwise unrelated. Plasminogen is a serine protease of the coagulation scheme that acts extracellularly, and LD is an intracellular oxidoreductase that is expressed in essentially all cells. Part of this sequence, Arg-Ile-Val-Gly-Gly, is conserved in the eukaryote serine proteases prothrombin, blood clotting factors IX, X, and XI, kallikrein, trypsinogen, chymotrypsinogen, and elastase, and also in bacterial trypsin (Dayhoff, M. O., Atlas of protein sequence and structure, Vol. 5 suppl. 3, Silver Spring, Md.: The National Biomedical Research Foundation (1978); Yoshitake, S. et al., *Biochemistry* 24:3736–50 (1985); Fujikawa, K. et al., *Biochemistry* 25:2417–24 (1986)). The arginine-isoleucine bond in this sequence is a common cleavage site for conversion of these molecules to activated forms.

EXAMPLE 6

Figure 4:
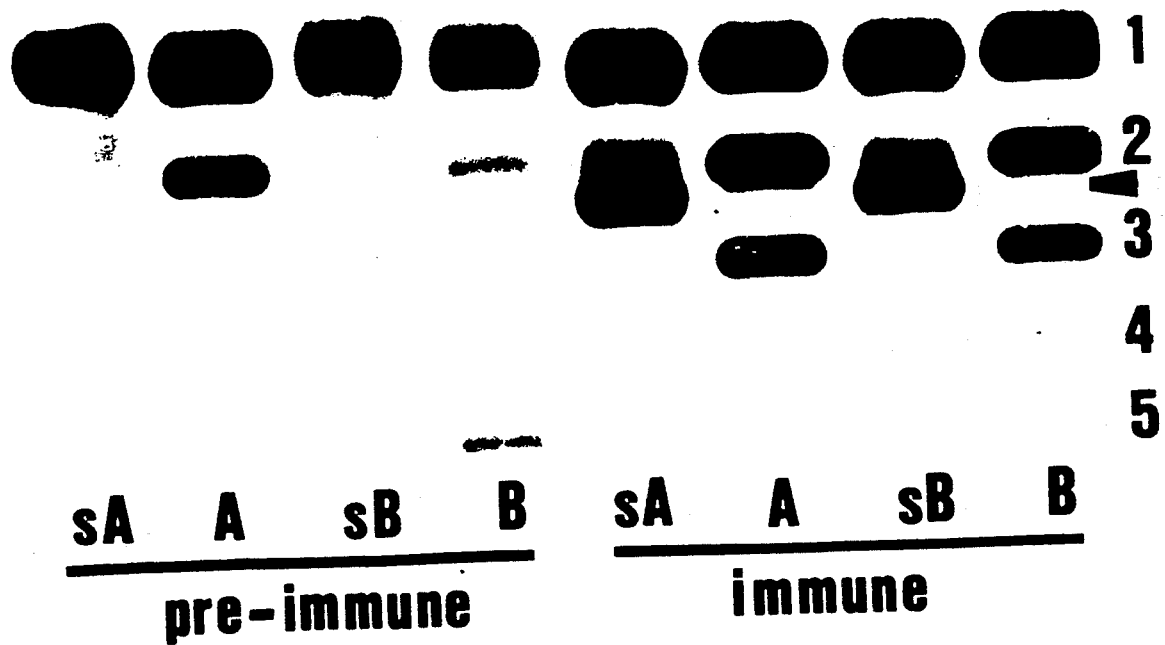
FIG. 4 is a gel electrophoretic pattern showing the assay of antistreptokinase antibodies in serum of rabbits. Rabbit "A" was immunized with 45,000 IU of streptokinase on day zero and 180,000 IU streptokinase on day 28. Rabbit "B" was immunized with 45,000 IU streptokinase on day zero. Serum was obtained from rabbits "A" and "B" prior to immunization and at day 40. Serum samples were electrophoresed in the Beckman Paragon$^R$ system either without the addition of streptokinase (lanes A and B in both the pre-immune and immune columns) or after a one hr incubation with 15,000 IU/ml final concentration (lanes sA and sB in both the pre-immune and immune columns). Arrow indicates the origin.

Detection of Antistreptokinase Antibodies With Streptokinase-LD Binding Activity Four New Zealand white rabbits were injected with streptokinase at days 0 and 28 to raise antibodies against streptokinase in the serum of the animals. Preimmune and immune serum samples were tested for the presence of anti-streptokinase antibodies by mixing the serum with 15,000 IU/ml streptokinase and LD electrophoresis as described above (FIG. 4). None of the preimmune samples tested showed LD precipitate at, or remain at, the origin of the gel. However, samples from rabbits that contained antistreptokinase antibodies at day 40 all had intense LD precipitates at the origin of the gel after addition of streptokinase to samples of their serum. LD isozymes which contain the M subunit all bound streptokinase as evidenced by the change in their migration but streptokinase atone did not result in a complex so big so as to precipitate at the electrophoretic origin. Neither preimmune sample, sA or sB, showed LD activity at the electrophoretic origin. Both immune sA and sB samples showed heavy LD activity at the origin.

EXAMPLE 7

Detection of Antistreptokinase Antibodies In Human Serum

Figure 5:
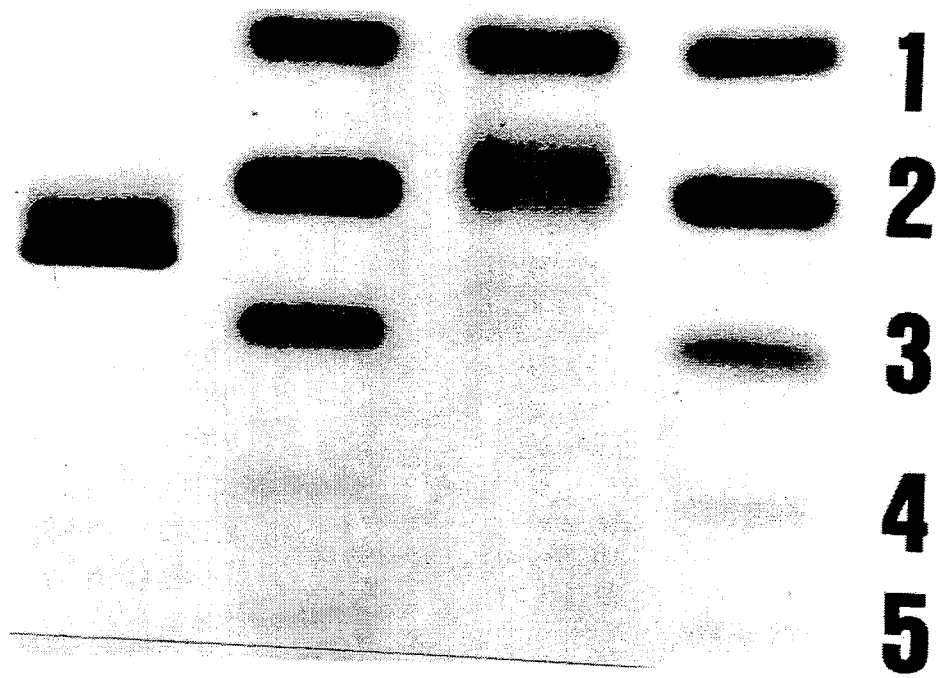
FIG. 5 is a gel electrophoretic pattern$_n$ showing the assay of antistreptokinase antibodies in human serum. Lane 1, sample A mixed with streptokinase; lane 2, sample A alone; the presence of a precipitate at the electrophoretic origin of lane 1 indicates that the serum contains antistreptokinase antibodies. Lane 3, sample B mixed with streptokinase; lane 4, sample B alone; there is no precipitate at the electro-phoretic origin of lane 3, therefore, the serum does not contain antistreptokinase antibodies. Arrow indicates the origin.

Serum samples from 43 patients were collected and used to assay for the presence of antistreptokinase antibodies by the addition of streptokinase and LD detection methodology. One part streptokinase (Kabikinase, Kabivitrum, Inc.) was mixed with 9 parts of serum to a final streptokinase concentration of 15,000 IU/ml, incubated for 1 hour, and electrophoresed according to the manufacturer's instructions on a Paragon LD Gel Electrophoresis system (Beckman). Total LD activity was also measured in these serum samples with the Hitachi 737 system (Boehringer Mannheim) before and after addition of streptokinase. Samples from 17 patients showed a heavy band (precipitate) of LD activity which remained at the electro-phoretic origin (FIG. 5). All samples showed alteration in migration of some LD isozymes. The samples with precipitates of LD at the origin also showed substantial loss of total LD activity. An average of 60% of the original activity was retained. Those samples with no precipitate at the gel origin lost very ilttle LD activity (95% of the activity was retained) (Table 2).

These results demonstrate that binding of anti-streptokinase antibodies to a streptokinase-LD complex and detection of the complex can be used to predict the presence of antistreptokinase antibodies in serum.

TABLE 2

| Assay of LD Activity in Serum After Addition of Streptokinase | | |
|---|---|---|
| Before Streptokinase | After Streptokinase | % original activity |
| AMBULATORY PATIENTS WITH LD PRECIPITATE | | |
| 338 | 47 | 14 |
| 162 | 52 | 32 |
| 357 | 292 | 82 |
| 174 | 159 | 91 |
| 210 | 199 | 95 |
| 171 | 93 | 54 |
| 221 | 172 | 78 |
| 172 | 69 | 40 |
| 179 | 122 | 68 |
| 249 | 227 | 91 |
| 348 | 311 | 89 |
| 171 | 34 | 20 |
| 125 | 19 | 15 |
| 350 | 294 | 84 |
| 309 | 220 | 71 |
| 198 | 125 | 63 |
| 363 | 134 | 37 |
| Average activity retained = | | 60% |
| AMBULATORY PATIENTS WITH NO LD PRECIPITATE | | |
| 181 | 176 | 97 |
| 64 | 61 | 95 |
| 270 | 269 | 100 |
| 179 | 176 | 98 |
| 193 | 189 | 98 |
| 233 | 232 | 100 |
| 189 | 193 | 102 |
| 230 | 221 | 96 |
| 145 | 140 | 97 |
| 161 | 157 | 98 |
| 225 | 213 | 93 |
| 174 | 172 | 99 |
| 183 | 179 | 98 |
| 213 | 172 | 81 |
| 215 | 216 | 100 |
| 382 | 265 | 69 |
| 144 | 105 | 77 |
| 120 | 122 | 102 |
| 194 | 188 | 97 |
| 199 | 199 | 100 |
| 176 | 162 | 92 |
| 269 | 255 | 95 |
| 227 | 230 | 101 |
| 252 | 238 | 94 |
| 137 | 125 | 91 |
| 762 | 742 | 97 |
| Average activity retained = | | 95% |

EXAMPLE 8

Streptokinase Dependent Inhibitor of Lactate Dehydrogenase Isoenzyme 5

The addition of streptokinase (STK) markedly decreased lactate dehydrogenase (LD; EC 1.1.1.27) activity in some serum samples (*Clin. Chem.* 35:1119 (1989)).

As described in this example, this phenomenon is due to the presence of anti-streptokinase antibodies which are specifically anti-complex antibodies in the serum samples. In order to study the frequency and partially characterize this phenomenon, serum or plasma samples were screened for differences in LD activity (Hitachi 737; Boehringer Mannheim Diagnostics) before and after addition of 15,000 IU/L STK (Kabinkinase, Kabivitrum). Of 178 samples, 7 (4%) showed inhibition of greater than 80% (average=89%) by addition of STK. Purified LD5 which was added to these samples demonstrated a stoichiometric relation between inhibition of LD5 activity and the presence of antistreptokinase antibodies. LD5 was purified by sequential Sephadex ® G-200 gel filtration, QAE-Sephadex ® chromatography and DEAE HPLC to yield a product with 280 U/mg specific activity. This material was stored at 4° C. until use. In timed studies, inhibition occurred rapidly with the majority completed within 5 minutes. Increasing amounts of purified LD5 were plated added to a fixed volume of plasma from a volunteer blood donor with initial inhibition of 90% of original activity. Plasma volumes of 20 (A), 30 (B), and 50 (C) mcL respectively inhibited 80 (A), 127 (B) and 217 (C) U/L of LD5 before ability to further inhibit was exhausted (plateau). The ratios showed below of different plasma concentrations were almost identical to the ratios of the maximum inhibited LD5 activity in different mixtures:

Plasma concentration ratios: A/B=0.67, A/C=0.40, B/C=0.60

Maximum inhibition ratios: A/B=0.63, A/C=0.37, B/C=0.59

This data indicates the inhibition of LD5 by STK is stoichiometrically mediated by the presence of anti-streptokinase antibodies in the patient's serum. Scatchard plot analysis of the data yield an affinity constant of $2.5 \times 10^9$ L/mol.

EXAMPLE 9

New Methods for Detection of Anti-streptokinase Antibodies

Anti-streptokinase antibodies (anti-STK) show considerable inter-individual titer difference, and the highest ones are able to neutralize streptokinase (STK) fibrinolytic therapy for acute myocardial infarction. Three methods for the detection of high titer anti-STK to guide choice of fibrinolytic drug have been developed. These include two standard methods (ELISA and fibrinolysis neutralization) and one using lactate dehydrogenase (LD:EC1.1.1.27) isoenzyme electrophoresis for rapid detection, based on the observations that STK binds to LD subunit M (*Clin. Chem.* 35:69 (1989)) and that anti-STK further alters electrophoretic pattern (*Clin. Chem.* 35:1119 (1989)). For ELISA, microtiter plates coated with 1 μg STK/well were incubated with diluted sample and then incubated with alkaline phosphatase-conjugated goat anti-human IgG to permit binding of the anti-IgG to any IgG present in the sample before color development-with p-nitrophenyl phosphate (405 nm). A positive value was >0.06 for plasma and >0.08 for serum. Fibrinolysis neutralization was done by mixing STK with plasma then added to wells in a 1% agarose plate containing 13% citrated plasma. After diffusion, gels were soaked in 0.05M CaCl$_2$. Reduction in lysis zone was a positive result. For LD isoenzyme pattern alteration (LD-STK), STK was added before electrophoresis. A positive result was a tight LD band at the origin, a wide band between LD2 and LD3, or marked decrease in LD activity. The fibrinolytic assay showed general agreement with ELISA establishing validity of ELISA. Of 60 patient samples, 43 were concordant and 17 discordant between ELISA and STK-LD. Only 2 of 20 serum samples were discordant. Four of 6 false negatives by STK-LD had high Lp(a) concentrations. Ten of 11 false positives were plasma samples. Detection of anti-STK by STK-LD correlates well with ELISA, although Lp(a) may interfere by competing for STK, and the preferred sample is serum. The strength of the STK-LD approach is its potential for use in acute care situations where rapid determinations are necessary for clinical utility.

While this invention has been described in detail and with reference to specific embodiments thereof, it will be apparent to one skilled in the art that various changes and modifications could be made therein without departing from the spirit and scope thereof.

What is claimed is:

1. A method for the detection and/or quantitation of antistreptokinase antibodies in a biological sample wherein said sample comprises lactate dehydrogenase subunit M (LD-M) which possesses affinity for streptokinase where said method comprises:
   (a) contacting said sample with a solution comprising streptokinase;
   (b) allowing said streptokinase to form a complex with said LD-M subunit and said antistreptokinase antibodies;
   (c) detecting and/or quantitating said complex between said LD-M streptokinase, and antistreptokinase antibodies; and
   (d) detecting and/or quantitating said antistreptokinase antibodies from the presence or amount of said complex.

2. A method for the detection and/or quantitation of antistreptokinase antibodies in a biological sample which comprises:
   (a) the addition of streptokinase to said biological sample;
   (b) binding of said streptokinase to LD-M subunit in said sample which possesses an affinity for said streptokinase;
   (c) detecting the isozyme pattern or quantitating the amount of LD-M in said sample; and
   (d) detecting and/or quantitating said antistreptokinase antibodies by said isozyme pattern or amount.

3. The method of either of claims 1 or 2, wherein said method further comprises electrophoresis of said sample following step (b) and before step (c).

4. The method of either of claims 1 or 2, wherein said method further comprises column chromatography of said sample following step (b) and before step (c).

5. The method of either of claims 1 or 2, wherein said method further comprises detecting said complex in step (c) by detecting the enzymatic activity of LD.

6. The method of either of claims 1 or 2, wherein said sample is serum.

7. The method of claim 6, wherein said serum is human serum.

8. The method of either of claims 1 or 2, wherein said antistreptokinase antibody recognizes uncomplexed streptokinase.

9. A method for the detection and/or quantitation of antistreptokinase antibodies in a biological sample wherein said sample comprises a protein either containing the streptokinase-binding sequence phe/cys-pro-lys- X-arg-val-ile/val-gly-X-gly-cys, wherein X can be any or no amino acid or containing a sequence with sufficient homology to said sequence so as to create affinity for streptokinase, which method comprises:
(a) contacting said sample with a solution comprising streptokinase;
(b) allowing said streptokinase to form a complex to form a complex with said protein and antistreptokinase antibodies wherein said protein is selected from the group selected from the group consisting of lactate dehydrogenase, plasminogen, plasmin and lipoprotein a;
(c) detecting and/or quantitating said complex between said protein, streptokinase, and
(d) detecting and/or quantitating said antistreptokinase antibodies from the presence or amount of said complex.

* * * * *

UNITED STATES PATENT AND TRADEMARK OFFICE
CERTIFICATE OF CORRECTION

PATENT NO. : 5,342,755

DATED : August 30, 1994

INVENTOR(S) : Podlasek et al.

It is certified that error appears in the above-indentified patent and that said Letters Patent is hereby corrected as shown below:

Column 1, line 9, delete "12" and insert therein --2--;line 43, delete "strop" and insert therein --strep--;line 65, delete "Bfogden" and insert therein --Brogden--.

Column 3, line 22, delete "is";line 26, delete "electro-phoretic" and insert therein --electrophoretic--;line 32, delete "semi -purified" and insert therein --semi-purified--;line 33, delete "semi -purified" and insert therein --semi-purified--;line 34, delete "al one" and insert therein --alone--.

Column 4, line 4, delete "$patter_n$" and insert therein --pattern--;line 11, delete "electro-phoretic" and insert therein --electrophoretic--.

Column 5, line 11, delete "tetramet" and insert therein --tetramer--;line 12, delete "tetramet" and insert therein --tetramer--.

Column 6, line 36, delete "p-nitro" and insert therein --$p$-nitro--.

Column 7, line 26, delete "tetramet" and insert therein --tetramer--.

Column 8, line 56, delete "Mannhelm" and insert therein --Mannheim--.

Column 10, line 24, delete "tetramet" and insert therein --tetramer--;line 65, delete "tetramet" and insert therein --tetramer--.

Column 11, Table 1, line 51, between rows "557-CYS" and "GLY" insert row --PRO   PRO PRO PRO PRO PRO PRO--.

UNITED STATES PATENT AND TRADEMARK OFFICE
CERTIFICATE OF CORRECTION

PATENT NO. : 5,342,755
DATED : August 30, 1994
INVENTOR(S) : Podlasek et al.

It is certified that error appears in the above-indentified patent and that said Letters Patent is hereby corrected as shown below:

Column 13, line 1, delete "complex" and insert therein --complexes--;line 28, between "this" and "sequence" insert --conserved--;line 49, delete "atone" and insert therein --alone--.

Column 14, line 3, delete "electro-phoretic" and insert therein --electrophoretic--;line 9, delete "ilttle" and insert therein --little--.

Column 15, line 7, delete "Mannhelm" and insert therein --Mannheim--;line 59, delete "p-nitrophenyl" and insert therein --*p*-nitrophenyl--.

Signed and Sealed this

Twenty-eight Day of February, 1995

Attest:

BRUCE LEHMAN

*Attesting Officer*     *Commissioner of Patents and Trademarks*